United States Patent
Washie et al.

(10) Patent No.: US 12,287,318 B2
(45) Date of Patent: Apr. 29, 2025

(54) WORKFLOW TO PREDICT SOURCE ROCK RICHNESS AND NET THICKNESS USING INTEGRATED INORGANIC, PYROLYSIS, AND WIRELINE DATA

(71) Applicant: SAUDI ARABIAN OIL COMPANY, Dhahran (SA)

(72) Inventors: Maimona Washie, Dhahran (SA); Fatai A. Anifowose, Al-Khobar (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 364 days.

(21) Appl. No.: 17/815,925

(22) Filed: Jul. 28, 2022

(65) Prior Publication Data

US 2024/0036022 A1    Feb. 1, 2024

(51) Int. Cl.
*G01N 33/24* (2006.01)
*E21B 49/00* (2006.01)
*E21B 49/02* (2006.01)

(52) U.S. Cl.
CPC ............. *G01N 33/24* (2013.01); *E21B 49/00* (2013.01); *E21B 49/02* (2013.01)

(58) Field of Classification Search
CPC ...... G01N 33/24; G01N 33/241; E21B 49/00; E21B 49/02; E21B 2200/20; E21B 2200/22

(Continued)

(56) References Cited

U.S. PATENT DOCUMENTS

| 7,013,972 B2 | 3/2006 | Vinegar et al. |
| 7,100,994 B2 | 9/2006 | Vinegar et al. |

(Continued)

FOREIGN PATENT DOCUMENTS

| CN | 103792592 A | 5/2014 |
| CN | 108717211 A | 10/2018 |

(Continued)

OTHER PUBLICATIONS

Gao et al., CN104278991A, "Saline Phase Hydrocarbon Source Rock Organic Carbon and Multi-component Well Logging Calculation Method of Hydrocarbon Latent Content", Date Published: Jan. 14, 2015 (Year: 2015).*

(Continued)

*Primary Examiner* — John H Le

(74) *Attorney, Agent, or Firm* — Osha Bergman Watanabe & Burton LLP

(57) ABSTRACT

A method to evaluate source rock richness is claimed. The method includes obtaining a source rock sample, collecting pyrolysis data from testing of the sample, filtering the pyrolysis data to produce a filtered pyrolysis data set, extracting a plurality of elements from their respective oxides and cross-checking the filtered pyrolysis data set with the plurality of elements. The method further includes discarding a plurality of unreliable data points from the filtered pyrolysis data set to produce a cross-checked data set, matching the cross-checked data set with wireline log data, determining a minimum value and a maximum value of the wireline log data that are within the cross-checked data set, and collecting depth thicknesses corresponding to the minimum value and the maximum value. The method also includes calculating a sum of the plurality of depth thicknesses, calculating a net source rock thickness, and calculating a corresponding average total organic carbon value.

20 Claims, 5 Drawing Sheets

(58) Field of Classification Search
USPC .......................................................... 702/11
See application file for complete search history.

(56) References Cited

U.S. PATENT DOCUMENTS

| | | | |
|---|---|---|---|
| 7,486,589 | B2 | 2/2009 | Lee et al. |
| 8,492,153 | B2 | 7/2013 | Jones et al. |
| 8,729,903 | B2 | 5/2014 | Srnka et al. |
| 10,408,962 | B2 | 9/2019 | Song |
| 2018/0347354 | A1 | 12/2018 | Li et al. |
| 2020/0408090 | A1 | 12/2020 | Kadayam Viswanathan et al. |
| 2021/0255358 | A1 | 8/2021 | Fawad et al. |
| 2022/0042413 | A1 | 2/2022 | Wang et al. |

FOREIGN PATENT DOCUMENTS

| | | |
|---|---|---|
| CN | 111949945 A | 11/2020 |
| CN | 113123780 A | 7/2021 |
| CN | 113589398 A | 11/2021 |

OTHER PUBLICATIONS

N. A. A. Edress et al.; "Geochemical characterization of the source rock intervals, Beni-Suef Basin, West Nile Valley, Egypt", Open Geosciences; vol. 13; Issue 1; Dec. 22, 2021; pp. 1536-1551 (16 pages).

Le Thi Nhut Suong et al.; "Application of Machine Learning Algorithms in Predicting Pyrolytic Analysis Result", IOP Conference Series: Earth and Environmental Science; vol. 931; 2021 (11 pages).

S. Jiang et al.; "Improving the Total Organic Carbon Estimation of the Eagle Ford Shale with Density Logs by Considering the Effect of Pyrite", Minerals; vol. 8; No. 154; Apr. 2018; pp. 1-12 (12 pages).

G. Scheeder et al.; "Geochemical implications from direct Rock-Eval pyrolysis of petroleum", Organic Geochemistry; vol. 146; May 26, 2020; pp. 1-11 (11 pages).

K. E. Peters; "Guidelines for Evaluating Petroleum Source Rock Using Programmed Pyrolysis", The American Association of Petroleum Geologists Bulletin; vol. 70; No. 3; Mar. 1986; pp. 318-329 (12 pages).

* cited by examiner

WORKFLOW TO PREDICT SOURCE ROCK RICHNESS AND NET THICKNESS USING INTEGRATED INORGANIC, PYROLYSIS, AND WIRELINE DATA

BACKGROUND

Petroleum source rock may refer to any rock sample with sufficient organic matter content to generate and release enough hydrocarbons to form a commercial accumulation of oil or gas. Source rocks are typically shales and lime mudstones. In petroleum exploration, it is crucial to perform an evaluation of petroleum source rocks and their corresponding hydrocarbon generation capabilities. A source rock's capability to generate hydrocarbons may also be referred to as source rock richness. Traditionally, source rock richness is assessed using pyrolysis, which is a tool used to analyze the presence of petroleum source rock and corresponding proportion of organic matter. Organic matter quantity is usually expressed as total organic carbon.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method to evaluate source rock richness. The method may include obtaining a source rock sample, collecting pyrolysis data from testing of the sample, filtering the pyrolysis data to produce a filtered pyrolysis data set, extracting a plurality of elements from their respective oxides and cross-checking the filtered pyrolysis data set with the plurality of elements. The method may further include discarding a plurality of unreliable data points from the filtered pyrolysis data set to produce a cross-checked data set, matching the cross-checked data set with wireline log data, determining a minimum value and a maximum value of the wireline log data that are within the cross-checked data set, and collecting depth thicknesses corresponding to the minimum value and the maximum value. The method may also include calculating a sum of the plurality of depth thicknesses, calculating a net source rock thickness, and calculating a corresponding average total organic carbon value.

In another aspect, embodiments disclosed herein relate to a non-transitory computer readable medium storing instructions executable by a computer processor. The instructions may include functionality for collecting pyrolysis data from testing of a source rock sample, filtering the pyrolysis data to produce a filtered pyrolysis data set, cross-checking the filtered pyrolysis data set with a plurality of elements, and discarding a plurality of unreliable filtered pyrolysis data points from the filtered pyrolysis data set to produce a cross-checked data set. The instructions may also include functionality for matching the cross-checked data set with wireline log data, determining a minimum value and a maximum value of the wireline log data that are within the cross-checked data set, and collecting a plurality of depth thicknesses corresponding to the minimum value and the maximum value. The instructions may further include functionality for calculating a total sum of the plurality of depth thicknesses, calculating a net source rock thickness, and calculating an average total organic carbon value corresponding to the net source rock thickness.

In yet another aspect, embodiments disclosed herein relate to a system, which may include a well, a wellbore extending through the well from a surface location to a downhole location, a wireline system disposed in the wellbore, and a computer processor located at the surface location. The computer processor may be configured to collect pyrolysis data from testing of a source rock sample, filter the pyrolysis data to produce a filtered pyrolysis data set, cross-check the filtered pyrolysis data set with a plurality of elements, and discard a plurality of unreliable filtered pyrolysis data points from the filtered pyrolysis data set to produce a cross-checked data set. The computer processor may also be configured to match the cross-checked data set with wireline log data, determine a minimum value and a maximum value of the wireline log data that are within the cross-checked data set, and collect a plurality of depth thicknesses corresponding to the minimum value and the maximum value. The computer processor may further be configured to calculate a total sum of the plurality of depth thicknesses, calculate a net source rock thickness, and calculate an average total organic carbon value corresponding to the net source rock thickness.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency. The size and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn are not necessarily intended to convey any information regarding the actual shape of the particular elements and have been solely selected for ease of recognition in the drawing.

DETAILED DESCRIPTION

Figure 1:
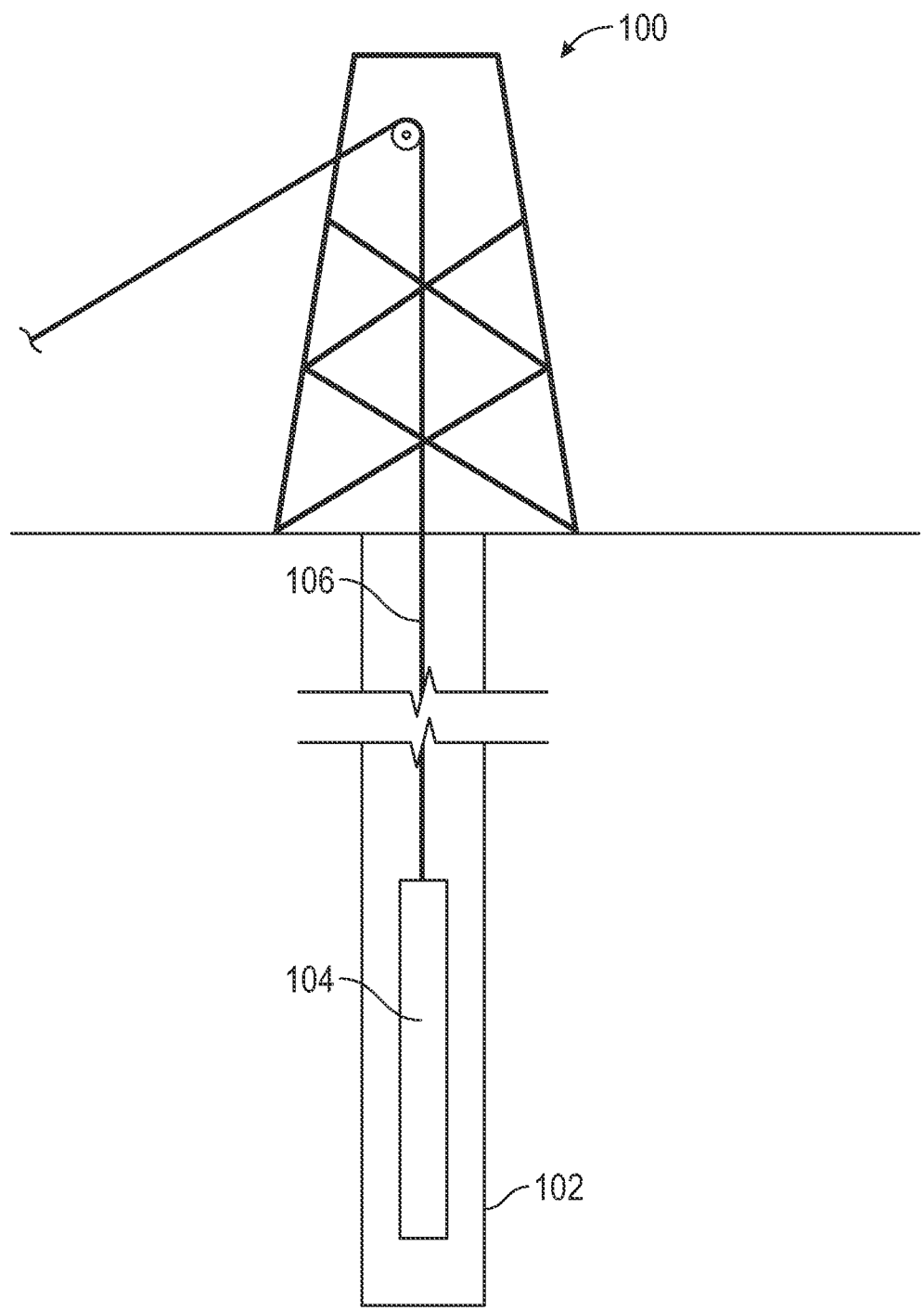
FIG. 1 shows a wireline equipment set up in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-5, any component described with regard to a figure, in various embodiments disclosed herein, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a seismic data set" includes reference to one or more of such seismic data set.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill that the subject matter of the dependent claims of one or more embodiments may be combined with other dependent claims.

The traditional pyrolysis tool may have a number of limitations. First, the abundance of pyrolysis data depends on the number of source rock samples analyzed. Since the number of source rock samples is generally limited, it is typically impossible to sample a multitude of sections across the entire well. Further, the volume of data acquired for sampled sections of the well is typically not enough to perform reliable testing. It is even more challenging to acquire such data for unsampled sections of the well, meaning that it is impossible to evaluate the source rock potential of the unsampled well sections. As such, there exists a need for a method of evaluating the source rock potential of unsampled well sections.

In one aspect, embodiments disclosed herein relate to a method of integrating pyrolysis data with inorganic and wireline log datasets to evaluate the source rock potential of unsampled sections of a well. In another aspect, embodiments disclosed herein relate to a system which may be configured to evaluate the source rock potential of unsampled sections of a well. In yet another aspect, embodiments disclosed herein relate to a non-transitory computer readable medium storing instructions executable by a computer processor, where the instructions comprise functionality for evaluating source rock potential of unsampled sections of a well.

Referring to FIG. 1, an example wireline equipment set up 100 is shown. The wellbore 102 extends from the wellbore surface to a downhole location. The wellbore 102 receives a tool string 104 that is lowered into the wellbore by a wireline 106 that is tethered at the wellbore surface. The tool string 104 may include an assembly of several different tools required to perform a particular downhole operation. For example, the tool string 104 may include logging and measurement tools and sampling tools. While the wellbore 102 is shown as being perfectly cylindrical with ample space between the tool string 104 and walls of the wellbore 102, this may not always be the case. Wellbore walls can sustain damage or otherwise change shape over time and may protrude into the wellbore.

Figure 2:
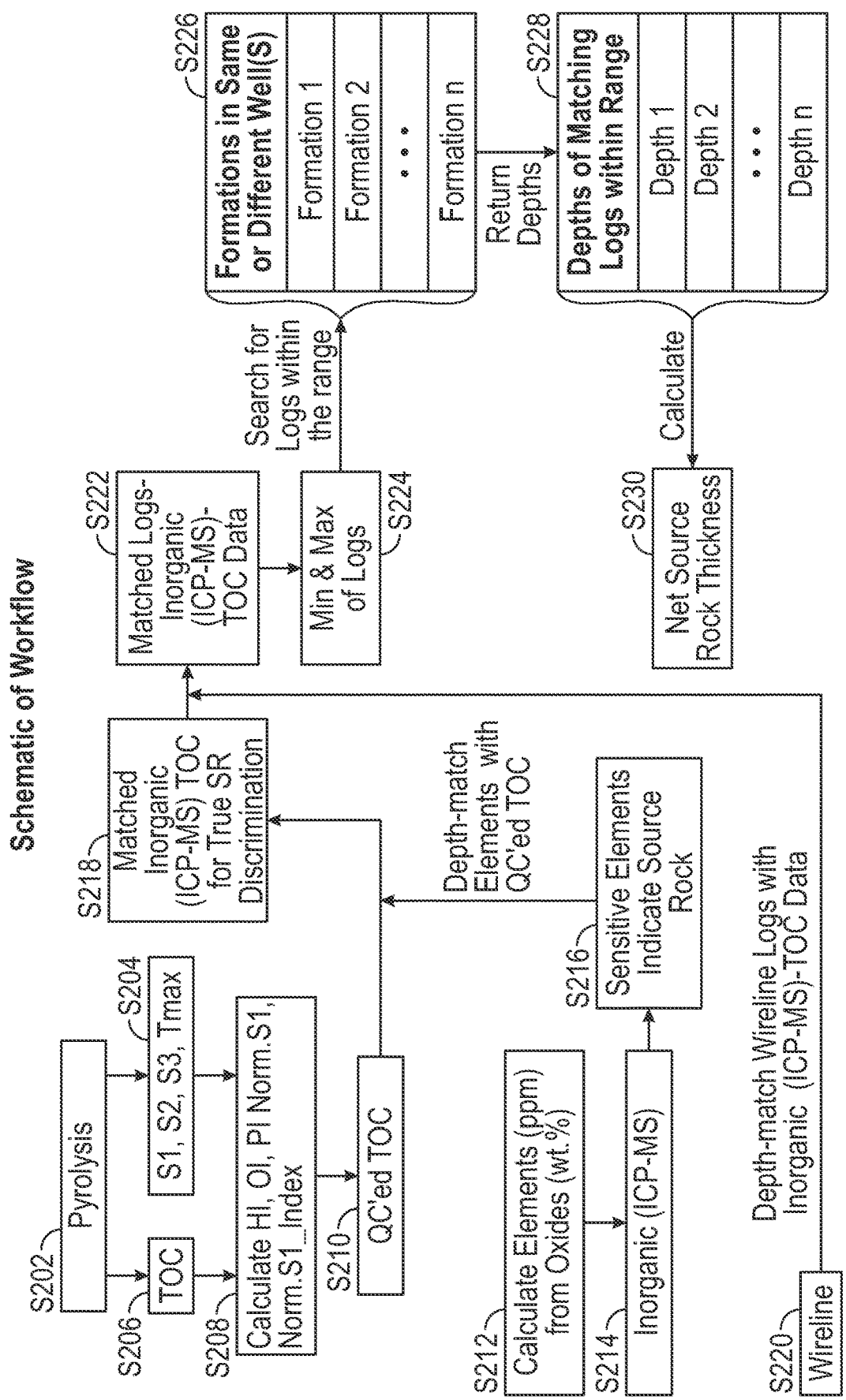
FIG. 2 shows a workflow schematic in accordance with one or more embodiments.

Turning now to FIG. 2, FIG. 2 shows a workflow schematic in accordance with one or more embodiments. Initially, the workflow may begin with acquiring pyrolysis data for one or more rock sample, S202. In one or more embodiments, pyrolysis data may include the following variables, S204: thermos-vaporized free hydrocarbon content (S1), genetic potential of the rock sample (S2), the quantity of evolved carbon dioxide per gram of rock in the sample (S3), and the temperature at which a peak S2 value occurs ($T_{max}$). Pyrolysis data may also include total organic carbon (TOC), which refers to the total amount of carbon in organic compounds, S206. In one or more embodiments, TOC may have the unit wt %.

In many situations, TOC data may be unreliable due to contamination. In one or more embodiments, contamination may be caused by drilling muds and additives. As such, it is beneficial to filter TOC data to remove the effects of possible contamination. In one or more embodiments, five filtration parameters may be calculated, as shown below in Equations 1-5, S208.

$$HI = \frac{S2}{TOC} * 100, \qquad \text{Equation 1}$$

where HI refers to the hydrogen index.

$$OI = \frac{S3}{TOC} * 100, \qquad \text{Equation 2}$$

where OI refers to the oxygen index.

$$PI = \frac{S1}{S1 * S2}, \qquad \text{Equation 3}$$

where PI refers to the production index.

$$Norm.S1 = \frac{S1}{TOC} * 100, \qquad \text{Equation 4}$$

where Norm.S1 refers to normalized S1.

$$Norm.S1\_Index = \frac{Norm.S1}{100}, \qquad \text{Equation 5}$$

where Norm.S1_Index refers to normalized S1 index.

The filtration parameters may be applied to the acquired TOC data as part of the following five numerical filters. First, any TOC values less than 0.5 wt % are likely not source rock. As such, the following filter may be applied, as shown in Equation 6:

$$TOC_{filtered} \Rightarrow TOC \Rightarrow 0.5, \quad \text{Equation 6}$$

In one or more embodiments, the application of Equation 6 may induce the discarding of any TOC data points which are less than 0.5 wt %.

A second filter may then be applied, which may assume that any data points where S2 is less than 1 are generally unreliable data points. As such, Equation 7 may be applied to $TOC_{filtered}$ in order to discard any unreliable data points from the data set:

$$TOC_{S2_{filtered}} \Rightarrow TOC_{filtered}(S2 \Rightarrow 1), \quad \text{Equation 7}$$

In one or more embodiments, a third filter may be applied to the TOC data, which may assume that any data points where the PI value is greater than 0.44 are unreliable data points. As such, Equation 8 may be applied in order to discard any unreliable data points from the data set:

$$TOC_{PI_{filtered}} \Rightarrow TOC_{S2_{filtered}}(PI < 0.44), \quad \text{Equation 8}$$

In one or more embodiments, a fourth filter may be applied to the TOC data, which may assume that any data points where Norm.S1 is greater than 100 are unreliable data points. As such, Equation 9 may be applied in order to discard any unreliable data points from the data set:

$$TOC_{S1.Norm_{filtered}} \Rightarrow TOC_{PI_{filtered}}(S1.\text{Norm}=<100), \quad \text{Equation 9}$$

In one or more embodiments, a fifth filter may be applied to the TOC data, which may assume that any data points where Norm.S1_Index is greater than 1 are unreliable data points. As such, Equation 10 may be applied in order to discard any unreliable data points from the data set:

$$TOC_{S1.Norm2_{filtered}} \Rightarrow TOC_{S1.Norm_{filtered}}(S1.\text{Norm}_{Index}=<1), \quad \text{Equation 10}$$

The final data set produced after the application of Equations 6-10 may be referred to as filtered TOC data or quality-checked TOC data, S210.

The quality-checked TOC data may be confirmed using elements from acquired inorganic data which are sensitive to the organic presence or anoxic depositional environment of the source rock samples. In one or more embodiments, the elements may be acquired using Inductively Coupled Plasma Mass Spectrometry (ICP-MS). In order to perform ICP-MS testing, elements must first be extracted from their respective oxides, S212. ICP-MS testing may then be performed on the extracted elements, S214, producing a plurality of elements sensitive to organic presence. In one or more embodiments, the presence of sensitive elements may indicate the presence of source rock in the rock sample, S216.

The quality-checked TOC data may then be plotted against the sensitive elements, allowing an operator to qualitatively confirm data points within the quality-checked TOC data set, S218. Performing such a cross-checking procedure may increase confidence in having true and accurate source rock intervals and may remove unreliable false flags in the data set. From the generated plot, data points from the quality-checked TOC data which correlate to low values of the sensitive elements may be considered unreliable and may therefore be discarded. A cross-checked TOC data set may thus be produced, where the cross-checked TOC data set contains a confirmed source rock interval. In one or more embodiments, the cross-checked TOC data set may also be referred to as a source rock richness data set, where richness refers to the reliability of the data set.

In one or more embodiments, a plurality of wireline logs may be obtained for the rock samples, S220. The wireline data logs may be matched with the cross-checked TOC data set, S222. Further, as a result of the matching, a maximum value and a minimum value of the logs which fall within the range of cross-checked TOC values are determined, S224. In one or more embodiments, the wireline logs may include sonic (DT), Deep Resistivity (RDEEP), Density (DT), (RHOB), Neutron Porosity (NPHI), Spectral Gamma Ray (SGR), Uranium (U), Thorium, Potassium, and Gamma Ray (GR) logs. For example, a combination of cross-checked TOC data and wireline logs may be displayed visually in a spreadsheet, as is shown in Table 1:

TABLE 1

| Depth [ft] | DT [US/F] | GR [GAPI] | NPHI [V/V] | RHOB [G/C3] | TOC_2 [wt %] |
|---|---|---|---|---|---|
| 10825.5 | 62.3173 | 31.3902 | 0.100364 | 2.5623 | |
| 10826 | 63.8383 | 38.229 | 0.112898 | 2.546 | |
| 10826.5 | 65.2647 | 47.182 | 0.128775 | 2.527 | 3.334 |
| 10827 | 66.361 | 58.0691 | 0.14029 | 2.5103 | |
| 10827.5 | 66.8153 | 63.8715 | 0.1465087 | 2.5037 | 4.65 |
| 10828 | 66.9307 | 58.0154 | 0.142843 | 2.5137 | |
| 10828.5 | 66.731 | 45.7126 | 0.130625 | 2.534 | |
| 10829 | 66.373 | 38.67 | 0.121167 | 2.5483 | |
| 10829.5 | 65.702 | 39.3409 | 0.121013 | 2.5477 | 3.14 |
| 10830 | 64.863 | 39.2918 | 0.124617 | 2.543 | |
| 10830.5 | 64.064 | 33.9059 | 0.121675 | 2.5517 | 6.21 |
| 10831 | 63.553 | 28.6197 | 0.111097 | 2.574 | |
| 10831.5 | 63.4543 | 29.6376 | 0.10404 | 2.59 | |
| 10832 | 63.8437 | 37.1178 | 0.108996 | 2.5817 | |
| 10832.5 | 64.877 | 47.2396 | 0.125282 | 2.5527 | 4.54 |
| 10833 | 66.4783 | 56.5043 | 0.140723 | 2.5203 | |
| 10833.5 | 68.3517 | 63.8306 | 0.14833 | 2.497 | 4.44 |
| 10834 | 70.014 | 69.0481 | 0.153134 | 2.4827 | |
| 10834.5 | 71.2627 | 70.5289 | 0.159027 | 2.474 | |
| 10835 | 72.1167 | 66.6028 | 0.166791 | 2.4673 | |
| 10835.5 | 72.7737 | 59.0995 | 0.17279 | 2.4607 | 3.51 |
| 10836 | 73.1963 | 52.8101 | 0.17539 | 2.454 | |
| 10836.5 | 73.466 | 50.0686 | 0.175267 | 2.4483 | 3.19 |
| 10837 | 73.5203 | 48.6404 | 0.171102 | 2.4463 | |
| 10837.5 | 73.4157 | 46.4158 | 0.162295 | 2.45 | 4.8 |
| 10838 | 72.9863 | 44.3342 | 0.154281 | 2.4593 | |

For example, in Table 1, highlighted portions indicate confirmed source rock intervals. Non-bolded areas, such as the interval between depth values 10831 and 10832, refer to non-source rock intervals.

The wireline logs of the entire well may then be scanned to determine the sections which fall within the estimated minimum and maximum log values. In one or more embodiments, scanning the wireline logs of the entire well may include considering a number of distinct formations within the same well, S226. The well sections determined to fall within the maximum and minimum log values may be without pyrolysis or inorganic data.

Depth points corresponding to log values matching the minimum and maximum log values are collected, S228. Depth points within a 1.5 ft distance of each other may be combined into a single interval. For example, if a first depth point and a second depth point are less than 1.5 ft apart, they may be included in the same interval. Depth points which are more than 1.5 ft from another depth point may be included in a separate interval. In one or more embodiments, there may be four depth points within an interval, where the spacing between each depth point is less than or equal to 1.5 feet. In such embodiments, the first depth point may be referred to as the 'top' and the fourth depth point may be referred to as the 'base'.

For example, referring back to Table 1, the first highlighted interval may be represented in Table 2, where the top is 10826.5 and the base is 10830.5. Total Source rock Thickness (TST) refers to the difference between the top and the base. In the previous example, the TST is equal to 4 ft. For each interval, an average $TOC_p$ value is calculated from the determined TOC_2 values included in Table 1. The total sum of the total source rock thicknesses may then be calculated, which produces the net source rock thickness, S230. In one more embodiments, data points may be presented in a spreadsheet, such as the example provided in Table 2:

TABLE 2

| Well Name | Top | Base | TST/ft | $TOC_p$/wt % |
|---|---|---|---|---|
| | 10801 | 10803.5 | 2.5 | |
| | 10806 | 10807.5 | 1.5 | |
| | 10812.5 | 10816.5 | 4 | |
| | 10826.5 | 10830.5 | 4 | 4.34 |
| | 10832.5 | 10870.5 | 38 | 6.8 |
| | 10874 | 10877.5 | 3.5 | |
| Total | | | 53.5 | 5.57 |

Figure 3:
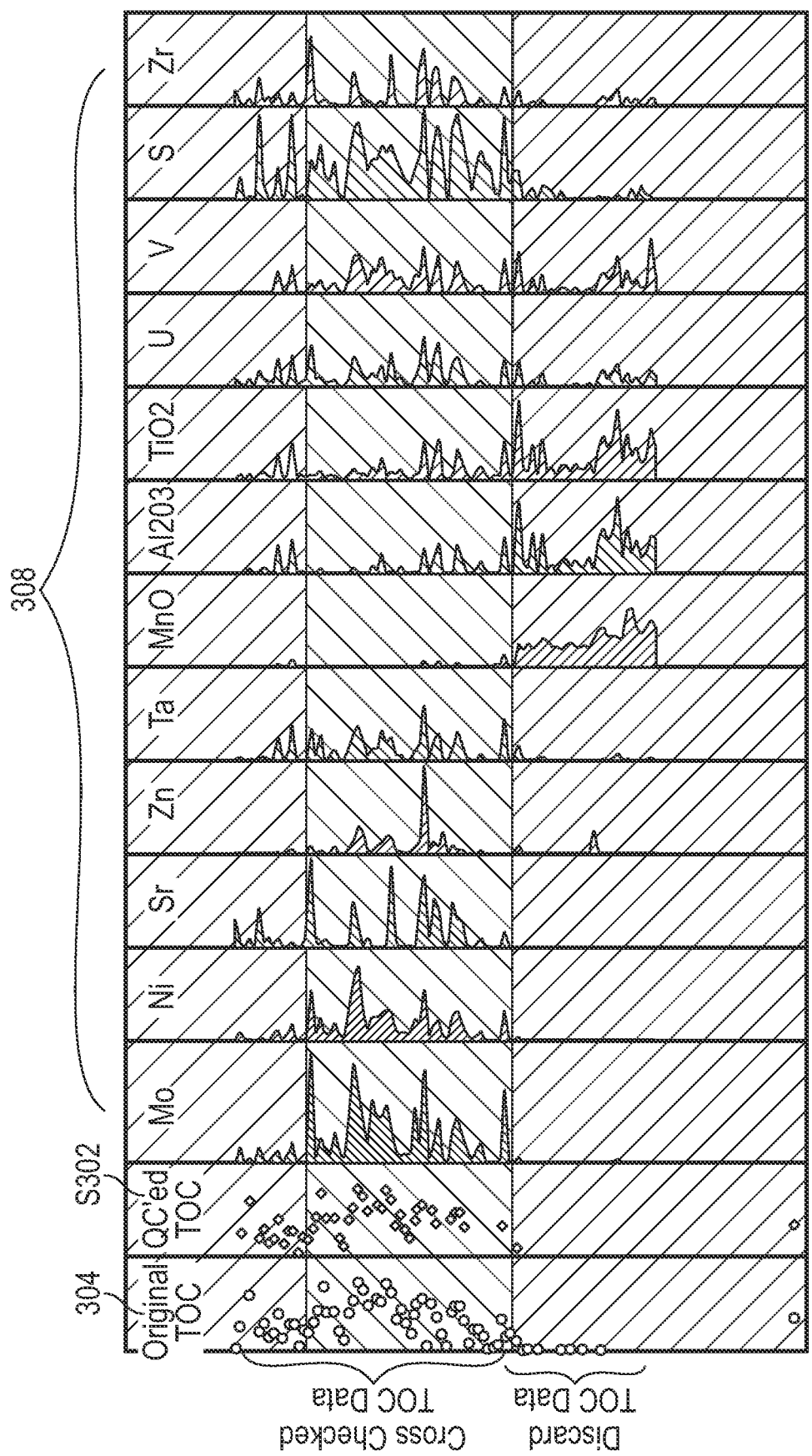
FIG. 3 shows a cross-checking tool in accordance with one or more embodiments.

FIG. 3 shows a cross-checking tool in accordance with one or more embodiments. Quality-checked TOC data may be plotted against a plurality of sensitive elements in order to further refine the dataset. For example, the quality-controlled TOC data set 302 has a smaller range than the original TOC data 304 due to the application of numerical filters. Following application of numerical filters, unreliable data points 306 are discarded. Once sensitive elements have been extracted from their respective oxides, they may be subjected to ICP-MS testing, where element quantities are acquired. Cross-checked TOC data may be obtained by plotting quality-checked TOC data alongside sensitive element quantities 308. TOC values which correlate to low quantities of the sensitive elements may be discarded. The cross-checked TOC data set correlates to a confirmed source rock interval.

Figure 4:
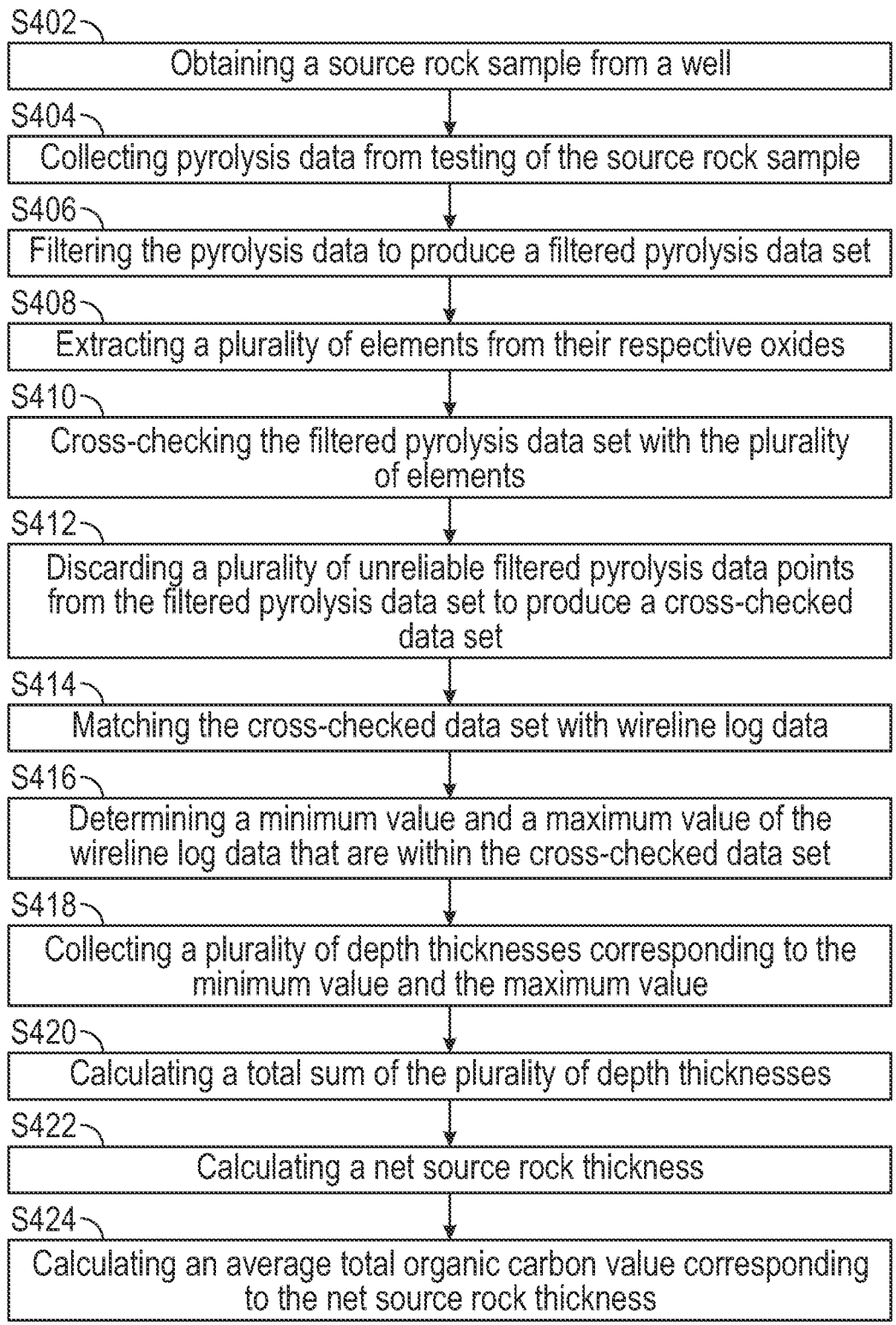
FIG. 4 shows a flowchart of a method in accordance with one or more embodiments.

FIG. 4 depicts a flowchart in accordance with one or more embodiments. More specifically, FIG. 4 depicts a flowchart 400 of a method of calculating an average total organic carbon value corresponding to the net source rock thickness. Further, one or more blocks in FIG. 4 may be performed by one or more components as described in FIGS. 1-3. While the various blocks in FIG. 4 are presented and described sequentially, one of ordinary skill in the art will appreciate that some or all of the blocks may be executed in different orders, may be combined, may be omitted, and some or all of the blocks may be executed in parallel. Furthermore, the blocks may be performed actively or passively.

Initially, a source rock sample may be obtained from a well, S402. In one or more embodiments, a plurality of source rock samples may be obtained. Pyrolysis data may be collected from testing the source rock sample, S404. In one or more embodiments, the pyrolysis data may include S1, S2, S3, $T_{max}$ and TOC data. However, in many situations, pyrolysis data may contain contamination caused by the presence of drilling muds or additives in the rock sample.

In one or more embodiments, the pyrolysis data may be filtered to remove any contamination from the data set, producing a filtered pyrolysis data set, S406. Any data points from the data set which do not meet the requirements of the numerical filters applied may be discarded.

The filtered pyrolysis data set may be further refined via a cross-checking procedure. In one or more embodiments, a plurality of elements may extracted from their respective oxides, S408. The extracted elements may then undergo ICP-MS testing to determine element quantities. In one or more embodiments, the extracted elements are elements which are sensitive to organic presence, indicating the presence of source rock. An operator may then plot the filtered pyrolysis data against the sensitive elements as a method of cross-checking the filtered pyrolysis data set, S410. Any data points in the filtered pyrolysis data set which correlate with low, or no, presence of the sensitive elements are considered to be unreliable and are discarded, S412. In one or more embodiments, the operator may assign a minimum acceptable limit for element presence, any data points below which will be discarded. The resulting data set may be referred to as a cross-checked data set. In one or more embodiments, the cross-checked data may also be referred to as a source rock richness data set. Richness, in such embodiments, refers to the accuracy of a data set, where the data set has been filtered to removed unreliable data points.

In one or more embodiments, wireline logs for the source rock sample may be obtained. In some embodiments, the wireline log data may be obtained in a laboratory setting. An operator may then match the cross-checked data set with the wireline log data, S414. A minimum value and a maximum value of the wireline data may be determined, where both the minimum value and the maximum value are located within the cross-checked data set, S416. Once a maximum and minimum value are determined, wireline logs of the entire well from which the rock sample was acquired may be scanned to determine well sections which fall between the maximum and minimum values.

A plurality of depth thickness corresponding to the maximum and minimum log values are collected, S418. Further, a total sum of the plurality of depth thicknesses may be calculated, S420. Net source rock thickness and a corresponding average TOC value may also be calculated, S422, S424.

In one or more embodiments, source rock richness may be used to estimate net source rock thickness. The signature of the source rock richness may be embedded in the wireline log data, where the maximum and minimum values (and the range there between) corresponding to the cross-checked data set were determined. In one or more embodiments, this may indicate true source rock potential. This range may be utilized to search in sections of the well where there may or may not be TOC data. As such, net source rock thickness may be estimated across a wider interval of investigation.

Figure 5:
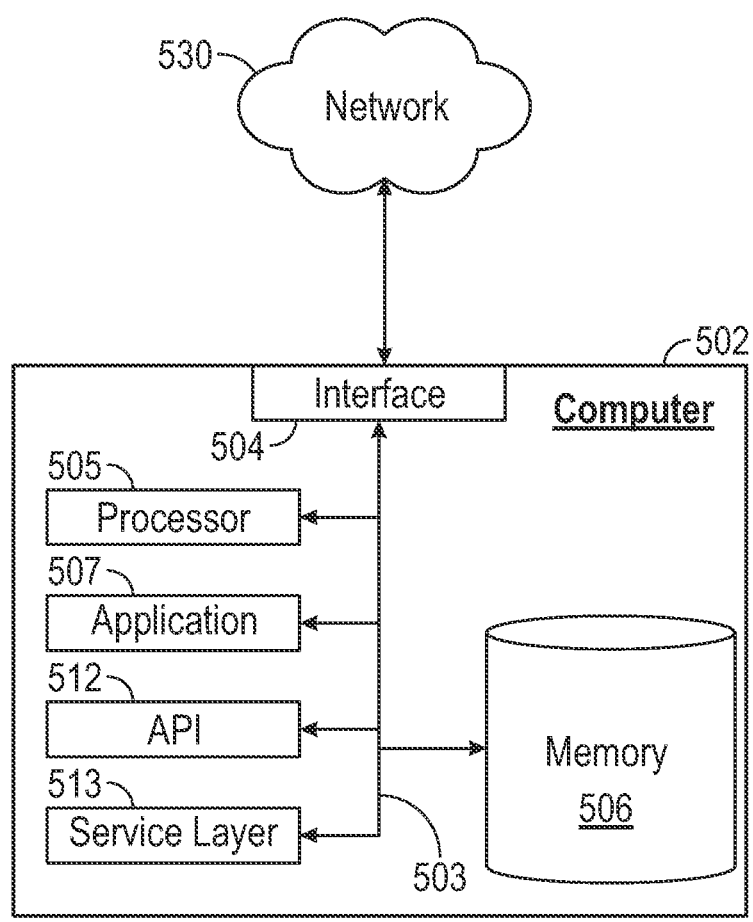
FIG. 5 shows a computer system in accordance with one or more embodiments.

FIG. 5 depicts a block diagram of a computer system 502 used to provide computational functionalities associated with described algorithms, methods, functions, processes, flows, and procedures as described in this disclosure, according to one or more embodiments. The illustrated computer 502 is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer 502 may include a computer that includes an input device, such as a keypad, keyboard, touch screen, or other device that can accept user information, and an output device that conveys information associated with the operation of the computer 502, including digital data, visual, or audio information (or a combination of information), or a GUI.

The computer 502 can serve in a role as a client, network component, a server, a database or other persistency, or any other component (or a combination of roles) of a computer system for performing the subject matter described in the instant disclosure. The illustrated computer 502 is communicably coupled with a network 530. In some implementations, one or more components of the computer 502 may be configured to operate within environments, including cloud-computing-based, local, global, or other environment (or a combination of environments).

At a high level, the computer 502 is an electronic computing device operable to receive, transmit, process, store, or manage data and information associated with the described subject matter. According to some implementations, the computer 502 may also include or be communicably coupled with an application server, e-mail server, web server, caching server, streaming data server, business intelligence (BI) server, or other server (or a combination of servers).

The computer 502 can receive requests over network 530 from a client application (for example, executing on another computer 502) and responding to the received requests by processing the said requests in an appropriate software application. In addition, requests may also be sent to the computer 502 from internal users (for example, from a command console or by other appropriate access method), external or third-parties, other automated applications, as well as any other appropriate entities, individuals, systems, or computers.

Each of the components of the computer 502 can communicate using a system bus 503. In some implementations, any or all of the components of the computer 502, both hardware or software (or a combination of hardware and software), may interface with each other or the interface 504 (or a combination of both) over the system bus 503 using an application programming interface (API) 512 or a service layer 513 (or a combination of the API 512 and service layer 513. The API 512 may include specifications for routines, data structures, and object classes. The API 512 may be either computer-language independent or dependent and refer to a complete interface, a single function, or even a set of APIs. The service layer 513 provides software services to the computer 502 or other components (whether or not illustrated) that are communicably coupled to the computer 502. The functionality of the computer 502 may be accessible for all service consumers using this service layer. Software services, such as those provided by the service layer 513, provide reusable, defined business functionalities through a defined interface. For example, the interface may be software written in JAVA, C++, or other suitable language providing data in extensible markup language (XML) format or another suitable format. While illustrated as an integrated component of the computer 502, alternative implementations may illustrate the API 512 or the service layer 513 as stand-alone components in relation to other components of the computer 502 or other components (whether or not illustrated) that are communicably coupled to the computer 502. Moreover, any or all parts of the API 512 or the service layer 513 may be implemented as child or sub-modules of another software module, enterprise application, or hardware module without departing from the scope of this disclosure.

The computer 502 includes an interface 504. Although illustrated as a single interface 504 in FIG. 5, two or more interfaces 504 may be used according to particular needs, desires, or particular implementations of the computer 502. The interface 504 is used by the computer 502 for communicating with other systems in a distributed environment that are connected to the network 530. Generally, the interface 504 includes logic encoded in software or hardware (or a combination of software and hardware) and operable to communicate with the network 530. More specifically, the interface 504 may include software supporting one or more communication protocols associated with communications such that the network 530 or interface's hardware is operable to communicate physical signals within and outside of the illustrated computer 502.

The computer 502 includes at least one computer processor 505. Although illustrated as a single computer processor 505 in FIG. 5, two or more processors may be used according to particular needs, desires, or particular implementations of the computer 502. Generally, the computer processor 505 executes instructions and manipulates data to perform the operations of the computer 502 and any machine learning networks, algorithms, methods, functions, processes, flows, and procedures as described in the instant disclosure.

The computer 502 also includes a memory 506 that holds data for the computer 502 or other components (or a combination of both) that can be connected to the network 530. For example, memory 506 can be a database storing data consistent with this disclosure. Although illustrated as a single memory 506 in FIG. 5, two or more memories may be used according to particular needs, desires, or particular implementations of the computer 502 and the described functionality. While memory 506 is illustrated as an integral component of the computer 502, in alternative implementations, memory 506 can be external to the computer 502.

The application 507 is an algorithmic software engine providing functionality according to particular needs, desires, or particular implementations of the computer 502, particularly with respect to functionality described in this disclosure. For example, application 507 can serve as one or more components, modules, applications, etc. Further, although illustrated as a single application 507, the application 507 may be implemented as multiple applications 507 on the computer 502. In addition, although illustrated as integral to the computer 502, in alternative implementations, the application 507 can be external to the computer 502.

There may be any number of computers 502 associated with, or external to, a computer system containing a computer 502, wherein each computer 502 communicates over network 530. Further, the term "client," "user," and other appropriate terminology may be used interchangeably as appropriate without departing from the scope of this disclosure. Moreover, this disclosure contemplates that many users may use one computer 502, or that one user may use multiple computers 502.

Embodiments of the present disclosure may provide at least one of the following advantages. In present approaches, wireline log data alone is typically used to predict total organic carbon. However, integrating multiple data sources and types allows for more accurate workflows and results. Further using the sensitivity of inorganic data to the organic presence or anoxic depositional environment of source rocks is largely absent from traditional approaches. Implementation of such a different method allows for more robust results, with the method allowing for the removal of potential false flags in the data set. Additionally, the use of numerical filters further improves accuracy of data for use in the rest of the workflow.

Obtaining net source rock thickness can assist with identifying source rock presence in a study area and determining an extent of source rock presence in the study area. Further, net source rock thickness also assists in validating source rock gross depositional environment (GDE) maps using the extent of source rock presence and estimating a hydrocarbon generation potential of a rock sample.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method to evaluate source rock richness, comprising:
   obtaining a source rock sample from a first rock interval of a well using a tool string comprising a rock sampling tool;
   collecting pyrolysis data from testing of the source rock sample using a pyrolysis tool;
   filtering, by a computer processor, the pyrolysis data using a first filter to produce a filtered pyrolysis data set, wherein the first filter is a total organic compound (TOC) filter that removed TOC data points from the pyrolysis data;
   extracting, from the source rock sample, a plurality of chemical elements from their respective oxides using Inductively Coupled Plasma Mass Spectrometry (ICP-MS);
   cross-checking, by the computer processor, the filtered pyrolysis data set with the plurality of chemical elements;
   discarding, by the computer processor, a plurality of unreliable filtered pyrolysis data points from the filtered pyrolysis data set using a second filter to produce a cross-checked data set;
   matching, by the computer processor, the cross-checked data set with wireline log data;
   determining, by the computer processor, a minimum value and a maximum value of the wireline log data based on matching the cross-checked data set with the wireline log data;
   collecting, by the computer processor, a plurality of depth thicknesses corresponding to the minimum value and the maximum value of the wireline log data;
   calculating, by the computer processor, a total sum of a source rock thickness using the plurality of depth thicknesses and the wireline log data;
   calculating, by the computer processor, a net source rock thickness based on a difference between a top and a base of a respective interval and the total sum of the source rock thickness; and
   calculating, by the computer processor, an average total organic carbon value corresponding to the net source rock thickness; and
   determining, by the computer processor, a hydrocarbon generation potential of a second rock interval based on the average total organic carbon value and the net source rock thickness,
   wherein the second rock interval is an unsampled well section of the well.

2. The method of claim 1, wherein the net source rock thickness comprises a continuous section of 1.5 feet.

3. The method of claim 1, wherein the plurality of chemical elements is selected from a group known to be sensitive to an organic presence or an anoxic depositional environment of source rocks.

4. The method of claim 1, wherein filtering the pyrolysis data comprises removing contamination from the pyrolysis data.

5. The method of claim 1, wherein the wireline log data comprises data produced by tests selected from a group consisting of sonic testing, deep resistivity testing, density testing, neutron porosity testing, spectral gamma ray testing, uranium testing, thorium testing, potassium testing and gamma ray testing.

6. The method of claim 1, wherein the pyrolysis data comprises total organic carbon (TOC), thermos-vaporized free hydrocarbon content (S1), genetic potential of a rock sample (S2), quantity of evolved carbon dioxide per gram of the rock sample (S3), and temperature at which a peak S2 value occurs (Tmax).

7. The method of claim 6, wherein filtering the pyrolysis data comprises:
   calculating a plurality of filter parameters; and
   applying a plurality of numerical filters to the pyrolysis data,
   wherein the plurality of numerical filters include the plurality of filter parameters.

8. The method of claim 7, wherein calculating the plurality of filter parameters comprises:
   calculating a hydrogen index (HI) value;
   calculating an oxygen index (OI) value;
   calculating a production index (PI) value;
   calculating a normalized S1 value; and
   calculating a normalized S1 index value.

9. The method of claim 1, further comprising integrating the pyrolysis data with a plurality of inorganic and wireline log data sets.

10. The method of claim 1, wherein cross-checking the filtered pyrolysis data set with the plurality of chemical elements comprises:
    plotting the filtered pyrolysis data set against the plurality of chemical elements; and
    assigning a minimum acceptable limit for data points within the filtered pyrolysis data set.

11. The method of claim 1, wherein the wireline log data is produced in a laboratory setting.

12. The method of claim 1, further comprising:
    identifying source rock presence in a study area;
    determining an extent of source rock presence in the study area;
    validating source rock gross depositional environment maps using the extent of source rock presence; and
    estimating a hydrocarbon generation potential of a rock sample.

13. A non-transitory computer readable medium storing instructions executable by a computer processor, the instructions being configured to perform a method comprising:

filtering pyrolysis data using a first filter to produce a filtered pyrolysis data set, wherein the first filter is a total organic compound (TOC) filter that removed TOC data points from the pyrolysis data,
  wherein the pyrolysis data is collected from testing of a source rock sample using a pyrolysis tool, and
  wherein the source rock sample is obtained from a first rock interval of a well using a tool string comprising a rock sampling tool;
cross-checking the filtered pyrolysis data set with a plurality of chemical elements,
  wherein the plurality of chemical elements are extracted from the source rock sample from their respective oxides using Inductively Coupled Plasma Mass Spectrometry (ICP-MS);
discarding a plurality of unreliable filtered pyrolysis data points from the filtered pyrolysis data set using a second filter to produce a cross-checked data set;
matching the cross-checked data set with wireline log data;
determining a minimum value and a maximum value of the wireline log data based on matching the cross-checked data set with the wireline log data;
collecting a plurality of depth thicknesses corresponding to the minimum value and the maximum value of the wireline log data;
calculating a total sum of a source rock thickness using the plurality of depth thicknesses and the wireline log data;
calculating a net source rock thickness based on a difference between a top and a base of a respective interval and the total sum of the source rock thickness; and
calculating an average total organic carbon value corresponding to the net source rock thickness; and
determining a hydrocarbon generation potential of a second rock interval based on the average total organic carbon value and the net source rock thickness,
  wherein the second rock interval is an unsampled well section of the well.

14. The non-transitory computer readable medium of claim 13, further comprising:
identifying source rock presence in a study area;
determining an extent of source rock presence in the study area;
validating source rock gross depositional environment maps using the extent of source rock presence; and
estimating a hydrocarbon generation potential of a rock sample.

15. The non-transitory computer readable medium of claim 13, wherein filtering the pyrolysis data comprises:
calculating a plurality of filter parameters; and
applying a plurality of numerical filters to the pyrolysis data,
  wherein the plurality of numerical filters include the plurality of filter parameters.

16. A system, comprising:
a well comprising a wellbore extending through the well from a surface location to a downhole location;
a pyrolysis tool;
a tool string comprising a rock sampling tool;
a wireline system disposed in the wellbore; and
a computer comprising a computer processor, wherein the computer is configured to perform a method comprising:
  filtering pyrolysis data using a first filter to produce a filtered pyrolysis data set,
    wherein the first filter is a total organic compound (TOC) filter that removed TOC data points from the pyrolysis data,
    wherein the pyrolysis data is collected from testing of a source rock sample using the pyrolysis tool, and
    wherein the source rock sample is obtained from a first rock interval of the well using the rock sampling tool of the tool string;
  cross-checking the filtered pyrolysis data set with a plurality of chemical elements,
    wherein the plurality of chemical elements are extracted from the source rock sample from their respective oxides using Inductively Coupled Plasma Mass Spectrometry (ICP-MS);
  discarding a plurality of unreliable filtered pyrolysis data points from the filtered pyrolysis data set using a second filter to produce a cross-checked data set;
  matching the cross-checked data set with wireline log data from the wireline system;
  determining a minimum value and a maximum value of the wireline log data based on matching the cross-checked data set with the wireline log data;
  collecting a plurality of depth thicknesses corresponding to the minimum value and the maximum value of the wireline log data;
  calculating a total sum of a source rock thickness using the plurality of depth thicknesses and the wireline log data;
  calculating a net source rock thickness based on a difference between a top and a base of a respective interval and the total sum of the source rock thickness; and
  calculating an average total organic carbon value corresponding to the net source rock thickness; and
  determining a hydrocarbon generation potential of a second rock interval based on the average total organic carbon value and the net source rock thickness,
    wherein the second rock interval is an unsampled well section of the well.

17. The system of claim 16, wherein the wireline system is configured to obtain wireline log data.

18. The system of claim 16, wherein the plurality of chemical elements is selected from a group known to be sensitive to an organic presence or an anoxic depositional environment of source rocks.

19. The system of claim 16, wherein filtering the pyrolysis data comprises removing contamination from the pyrolysis data.

20. The system of claim 16, wherein the wireline log data comprises data produced by tests selected from a group consisting of sonic testing, deep resistivity testing, density testing, neutron porosity testing, spectral gamma ray testing, uranium testing, thorium testing, potassium testing and gamma ray testing.

* * * * *